United States Patent [19]

Jung et al.

[11] Patent Number: 5,563,149
[45] Date of Patent: *Oct. 8, 1996

[54] AQUEOUS SOLUTIONS OF PYRIDONE CARBOXYLIC ACIDS

[75] Inventors: Yong H. Jung; Kyu J. Yeon, both of Seoul; Nam J. Baek, Kyunggi-do; Dong M. Lim, Anyang-city; Dal H. Kim, Soowun-city; Jae M. Lee, Seoul; Jin W. Kim, Sungnam-city, all of Rep. of Korea

[73] Assignee: Cheil Foods & Chemicals, Inc., Seoul, Rep. of Korea

[ * ] Notice: The term of this patent shall not extend beyond the expiration date of Pat. No. 5,527,910.

[21] Appl. No.: 287,265

[22] Filed: Aug. 8, 1994

[30] Foreign Application Priority Data

Jun. 8, 1994 [KR] Rep. of Korea ............... 1994-12975

[51] Int. Cl.$^6$ ............ A61K 31/435; A61K 31/47; C07D 215/56; C07D 471/04

[52] U.S. Cl. ............ 514/300; 514/312; 546/123; 546/156

[58] Field of Search ............ 546/123, 156; 514/312, 300

[56] References Cited

U.S. PATENT DOCUMENTS

| | | | |
|---|---|---|---|
| 4,988,709 | 1/1991 | Ogata | 514/314 |
| 5,164,402 | 11/1992 | Brighty | 514/300 |

*Primary Examiner*—C. Warren Ivy
*Assistant Examiner*—Evelyn Huang
*Attorney, Agent, or Firm*—Burns, Doane, Swecker & Mathis, L.L.P.

[57] ABSTRACT

Aqueous solutions of novel pyridone carboxylic acid compounds and esters or salts thereof having powerful antibacterial activities against both gram-negative and gram-positive bacteria, and in particular both ready-to-use injection and/or infusion solutions and dosage forms which can be converted into such injection and/or infusion solutions before use are disclosed.

4 Claims, No Drawings

AQUEOUS SOLUTIONS OF PYRIDONE CARBOXYLIC ACIDS

FIELD OF THE INVENTION

The invention relates to aqueous solutions of novel pyridone carboxylic acid compounds and esters or salts thereof having powerful antibacterial activities against both gram-negative and gram-positive bacteria, and in particular both ready-to-use injection and/or infusion solutions and dosage forms which can be converted into such injection and/or infusion solutions before use.

BACKGROUND OF THE INVENTION

The novel pyridone carboxylic acid compounds contained in an aqueous solution according to the present invention are described and claimed in pending U.S. patent application Ser. No. 08/160821 filed Dec. 3, 1993.

While a number of quinolone compounds such as Norfloxacin, Enoxacin, Ofloxacin, Ciprofloxacin and the like has been developed and proven successful in commerce owing to their potent and broad spectrum of antibacterial activities, much research has been conducted to increase the solubility of poorly soluble quinolone compounds in water. Many acids and bases which lead to the aqueous solution not only in which quinolone compounds were dissolved to the level that it may be suitable for injection or infusion but also whose shelf life is sufficiently long enough to fulfil the pharmaceutical requirements imposed on the injection and/or infusion.

Korean Patent Application Publication No. 87-1958 describes that the acids suitable for making the aqueous solutions of quinolone compounds include hydrochloric acid, methansulfonic acid, acetic acid, propionic acid, succinic acid and fumaric acid.

Korean Patent Application Publication No. 89-2040 describes examples of possible acids which do not lead to deposits of Norfloxacin and Enoxacin solutions, such as asparagine, glutamic acid and gluconic acid.

In Korean Patent Application Publication No. 89-2240, sodium hydroxide, potassium hydroxide, ethanolamine, lysine, N-methylglutamine and arginine are disclosed as examples of bases which do not lead to deposits in aqueous solutions of quinolone medicaments. However, the aqueous solution of quinolone compounds which is prepared using such bases as solubilizing agents is unsuitable or poorly very suitable for injection and/or infusion because the pH of the solution is too high.

U.S. Pat. No. 4,705,789 relates to solutions characterized by containing lactic acid salts of piperazinylquinolone- and piperazinylazaquinolone-carboxylic acids and at least one acid which does not lead to precipitates, in particular lactic acid.

U.S. Pat. No. 4,957,922 relates to aqueous infusion solutions comprising 1-cyclopropyl-6-fluoro-1,4-di-hydro-4-oxo- 7-(1-piperazinyl)-quinoline-3-carboxylic acid (=ciprofloxacin) and an amount of at least one physiologically tolerated acid which suffices to dissolve the active compound.

As the novel pyridone carboxylic acid compounds of formula I as represented below were in vitro evaluated about their efficacy, it was found that these compounds, especially 1-cyclopropyl-6-fluoro-1,4-dihydro-4-oxo-7-([1α, 5α,6β]6-amino-1-methyl-3-azabicyclo[3.2.0]heptan-3-yl)-1,8-naphtyridine-3-carboxylic acid(hereinafter "compound A") exhibit superior antibacterial activities to Lomefloxacin and Ofloxacin which are utilized for combating gram-negative and gram-positive bacteria and that these compounds including compound A has 2 to 16 times as much antibacterial activity as Ciprofloxacin, especially against gram-positive bacteria. Moreover, the novel pyridone carboxylic acid compounds, especially compound A show better bioavailability and half-life than drugs of quinolone compounds which either are commercially available or still on developments.

However, The novel pyridone carboxylic acid compounds including compound A as represented below have some difficulties in being formulated into aqueous solutions for injection and/or infusion, since it is not substantially soluble or little soluble in water as most known qunolone compounds having antibacterial activities are.

It was very suprising to find that by addition of hydrochloric acid, gluconic acid lactone, gluconic acid, malic acid, succinic acid, aspattic acid or mixtures thereof, it was possible to form injection and/or infusion solutions not only having higher amounts of the compounds of the formula I dissolved in water but also having appropriate pH and stability for the pharmaceutical requirements to be imposed on such solutions. Moreover, it was suprisingly found that when the combinations of at least one of the compounds of the formula I with the said acids were formulated into injection and/or infusion solutions, not only does the pH of the solutions maintain in the appropriate range for the administration but also no deposits form during storage in a long period.

Therefore, the object of the present invention is to provide aqueous solutions in which effective amounts of the compounds of the formula I as represented below were dissolved so as to be used as injection and/or infusion solutions.

SUMMARY OF THE INVENTION.

The present invention relates to aqueous solutions which can be converted into injection or infusion solutions, comprising at least one of acids as solubilizing agents, said acid being selected from the group consisting of gluconic acid lactone, gluconic acid, malic acid, succinic acid, aspattic acid and hydrochloric acid and, as active substances, at least one of the compounds of the formula I:

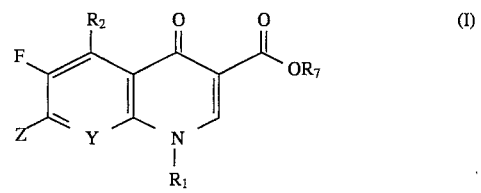

wherein
$R_1$ represents a lower alkyl, a halogen-substituted lower alkyl, a lower alkenyl, a cycloalkyl or a substituted or unsubstituted phenyl;
$R_2$ represents a hydrogen atom, a lower alkyl or an amino group;
Y represents a nitrogen atom or the group C-X in which X is a hydrogen, a halogen or an alkoxy group;
$R_7$ represents a hydrogen or a lower alkyl group; and Z is a group having the following formula:

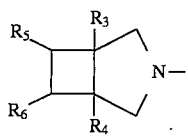

in which each of $R_3$ and $R_4$ represent independently a hydrogen or a lower alkyl group, with the proviso that one of $R_3$ and $R_4$ is a lower alkyl group; one of $R_5$ and $R_6$ is a hydrogen and another is a hydroxy, a lower alkoxy, or an amino group which is unsubstituted or substituted by a lower alkoxy or a lower alkyl group; and esters and salts thereof.

DETAILED DESCRIPTION OF THE INVENTION in a broad aspect, the aqueous solutions of the present invention comprise at least one of acids as solubilizing agents, said acid being selected from the group consisting of gluconic acid lactone, gluconic acid, malic acid, succinic acid, aspattic acid and hydrochloric acid and, as active substances, at least one of the compounds of the formula I as represented above. More specifically, the aqueous solutions produced in accordance with the present invention can be formed by combining at least one of the said acids and at least one of the active pyridone carboxylic acid compounds in the mole ratios of the acids to the active compounds between 0.5 and 6.0. Preferably, the mole ratios of the said acids to active pyridone carboxylic acid compounds according to the invention can be between 0.9 and 2.0, more preferably between 0.9 and 1.4. Then, the pH of the solution according to the invention can be between 2 and 8, preferably between 2.5 and 5.

As used herein, the term "solubilizing agent" means an auxiliary which aids effective amounts of quinolone compounds to be dissolved in water to form injection and infusion solutions. The term "halogen" includes chloro, bromo, and fluoro. The term "lower alkyl" may include, for example, methyl, ethyl, propyl, isopropyl, butyl, isobutyl, t-butyl, neopentyl, etc. The term "lower alkenyl" may include, for example, vinyl, allyl, 1-propenyl, and isopropenyl. The term "cycloalkyl" includes, for example, cyclopropyl, cyclobutyl, cyclopentyl, and cyclohexyl. The substituent for phenyl group may include, for example, a halogen atom, and a lower alkyl, lower alkoxy, halogen-lower alkyl, hydroxy, nitro and amino group. The term "alkoxy" includes, for example, methoxy, ethoxy, propoxy or butoxy group.

The organic acids suitable as solubilizing agents are chosen depending on the correlationship between the organic acid and the physical properties of the selected quinolone compound. Therefore, a varity of organic acids and amino acids were evaluated to determine whether certain acids are suitable as solubilizing agents capable of increasing the water solubility of compound A and the pH of the aqueous solution is suitable for injection and/or infusion solutions. As a result of such tests, it was shown that glutaric acid, cinnamic acid, galacturonic acid, glutamine, isoleusine, threonine, histidine, L-cysteine, alanine, arginine, L-valine, methionine and oxaline did not substantilly improve the solubility of compound A or the pH of the resulting solution is unsuitable as injection and/or infusion solutions.

Exemplary active substance in practicing the present invention is compound A. The test method of the solubility is set forth as follows:

Compound A was mixed with an organic acid or an amino acid in the mole ratios between 0.5 and 6 before water was added with reflux. Then, the resulting solution was rigorously shaken with stirring for 5 minutes so that it was made homogeneous. After the homogenous solution was left to stand at elevated temperature for 4 hours, it was extracted through 0.45 micro of membrane filter. The amounts of active substances present in extracts were quantified by high pressure liquid chromatography. The results of the test are reported in Table 1 below.

| EXAMPLE 1 | |
|---|---|
| 1-Cyclopropyl-6-fluoro-1,4-dihydro-4-oxo-7-([1α,5α,6β]6-amino-1-methyl-3-azabicyclo[3.2.0]heptan-3-yl)-1,8-naphtyridine-3-carboxylic acid (compound A) | 0.10 g |
| Glutamine | 0.04 g |
| Water to | 10.00 ml |
| EXAMPLE 2 | |
| Compound A | 0.10 g |
| Methionine | 0.04 g |
| Water to | 10.00 ml |
| EXAMPLE 3 | |
| Compound A | 0.10 g |
| L-valine | 0.04 g |
| Water to | 10.00 ml |
| EXAMPLE 4 | |
| Compound A | 0.10 g |
| L-cysteine | 0.14 g |
| water to | 10.00 ml |
| EXAMPLE 5 | |
| Compound A | 0.10 g |
| Alanine | 0.03 g |
| Water to | 10.00 ml |
| EXAMPLE 6 | |
| Compound A | 0.10 g |
| Arginine | 0.05 g |
| Water to | 10.00 ml |
| EXAMPLE 7 | |
| Compound A | 0.10 g |
| Asparagine | 0.04 g |
| Water to | 10.00 ml |
| EXAMPLE 8 | |
| Compound A | 0.10 g |
| Aspartic acid | 0.04 g |
| Water to | 10.00 ml |
| EXAMPLE 9 | |
| Compound A | 0.10 g |
| Isoleucine | 0.04 g |
| Water to | 10.00 ml |
| EXAMPLE 10 | |
| Compound A | 0.10 g |
| Threonine | 0.04 g |
| Water to | 10.00 ml |
| EXAMPLE 11 | |
| Compound A | 0.10 g |
| Histidine | 0.05 g |
| Water to | 10.00 ml |
| EXAMPLE 12 | |
| Compound A | 0.10 g |
| Cinnamic acid | 0.04 g |
| Water to | 10.00 ml |
| EXAMPLE 13 | |
| Compound A | 0.10 g |
| Galacturonic acid | 0.06 g |
| Water to | 10.00 ml |

-continued

EXAMPLE 14

| Compound A | 0.10 g |
| 1N hydrochloric acid | 0.34 g |
| Water to | 10.00 ml |

EXAMPLE 15

| Compound A | 0.10 g |
| Gluconic acid | 0.06 g |
| Water to | 10.00 ml |

EXAMPLE 16

| Compound A | 0.10 g |
| Glucuronic acid | 0.06 g |
| Water to | 10.00 ml |

EXAMPLE 17

| Compound A | 0.10 g |
| Malic acid | 0.04 g |
| Water to | 10.00 ml |

EXAMPLE 18

| Compound A | 0.10 g |
| Succinic acid | 0.04 g |
| Water | 10.00 ml |

EXAMPLE 19

| Compound A | 0.10 g |
| Gluconic acid lactone | 0.60 g |
| Water to | 10.00 ml |

EXAMPLE 20

| Compound A | 0.10 g |
| Oxalic acid | 0.04 g |
| Water to | 10.00 ml |

TABLE 1

| acids | solubility of compound A (mg/ml of water) | pH of saturated solution |
| --- | --- | --- |
| Glutamine | 1.6 | 6.4 |
| Methionine | 1.5 | 6.4 |
| L-valine | 1.3 | 6.4 |
| L-cysteine | 2.3 | 6.2 |
| Alanine | 1.3 | 6.4 |
| Arginine | 8.2 | 10.0 |
| Asparagine | 2.1 | 6.2 |
| Aspartic acid | 37.6 | 5.3 |
| Isoleucine | 1.4 | 6.4 |
| Threonine | 1.5 | 6.3 |
| Histidine | 2.1 | 7.6 |
| Galacturonic | 18.3 | 3.3 |
| Gluconic acid lactone | 28.1 | 3.6 |
| Gluconic acid | 33.4 | 3.3 |
| Glutaric acid | 12.1 | 3.8 |
| Malic acid | 48.7 | 3.4 |
| Succinic acid | 47.6 | 4.0 |
| Cinnamic acid | 2.1 | 1.8 |
| Hydrochloric acid | 44.3 | 2.0 |
| Oxalic acid | 3.5 | 4.2 |

What is claimed is:

1. An aqueous solution comprising at least one acid as a solubilizing agent, said acid being selected from the group consisting of gluconic acid lactone, gluconic acid, malic acid, succinic acid, aspartic acid and hydrochloric acid and at least one compound of the formula I:

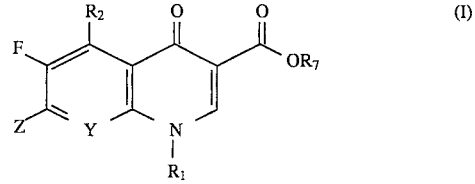

wherein $R_1$ represents a lower alkyl, a halogen-substituted lower alkyl, a lower alkenyl, a cycloalkyl or a substituted or unsubstituted phenyl;

$R_2$ represents a hydrogen atom, a lower alkyl or an amino group;

Y represents a nitrogen atom or the group C-X in which X is a hydrogen, a halogen or an alkoxy group;

$R_7$ represents a hydrogen or a lower alkyl group; and

Z is a group having the following formula:

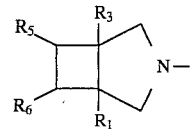

in which each of $R_3$ and $R_4$ represent independently a hydrogen or a lower alkyl group, with the proviso that one of $R_3$ and $R_4$ is a lower alkyl group; one of $R_5$ and $R_6$ is a hydrogen and another is a hydroxy, a lower alkoxy, or an amino group which is unsubstituted or substituted by a lower alkoxy or a lower alkyl group; and esters or salts thereof.

2. The aqueous solution according to claim 1, wherein the compound of formula I is 1-cyclopropyl-6-fluoro-1,4-dihydro-4-oxo-7-([1α,5α, 6β]6-amino-1-methyl-3-azabicyclo[3.2.0]heptan-3-yl)-1,8-naphtyridine-3-carboxylic acid.

3. The aqueous solution according to claim 1, wherein the mole ratio of the said solubilizing agent to the compound of formula I is between 0.5 and 6.0.

4. The aqueous solution according to claim 1, wherein said solution is an injection or infusion solution.

* * * * *